(12) United States Patent
Van Es et al.

(10) Patent No.: US 9,079,844 B2
(45) Date of Patent: Jul. 14, 2015

(54) CATALYTIC OXIDATION OF URONIC ACIDS TO ALDARIC ACIDS

(71) Applicant: Stichting Dienst Landbouwkundig Onderzoek, Wageningen (NL)

(72) Inventors: Daniël Stephan Van Es, Wageningen (NL); Jacobus van Haveren, Wageningen (NL); Henricus Wilhelmus Carolina Raaijmakers, Wageningen (NL); Frits van der Klis, Wageningen (NL); Gerardus Petrus Franciscus Maria van Engelen, Wageningen (NL); Augustinus Emmanuël Frissen, Wageningen (NL)

(73) Assignee: STICHTING DIENST LANDBOUWKUNDIG ONDERZOEK (NL)

( * ) Notice: Subject to any disclaimer, the term of this patent is extended or adjusted under 35 U.S.C. 154(b) by 0 days.

(21) Appl. No.: 14/390,211

(22) PCT Filed: Mar. 28, 2013

(86) PCT No.: PCT/NL2013/050234
§ 371 (c)(1),
(2) Date: Oct. 2, 2014

(87) PCT Pub. No.: WO2013/151428
PCT Pub. Date: Oct. 10, 2013

(65) Prior Publication Data
US 2015/0065749 A1 Mar. 5, 2015

(30) Foreign Application Priority Data
Apr. 4, 2012 (EP) .................................. 12163081

(51) Int. Cl.
*C07C 51/235* (2006.01)
*B01J 23/52* (2006.01)
*C07H 1/00* (2006.01)
*C07H 7/033* (2006.01)
*C07C 59/285* (2006.01)
*B01J 23/66* (2006.01)
*B01J 21/04* (2006.01)
*B01J 21/06* (2006.01)

(52) U.S. Cl.
CPC ............... *C07C 51/235* (2013.01); *B01J 23/52* (2013.01); *B01J 23/66* (2013.01); *C07C 59/285* (2013.01); *C07H 1/00* (2013.01); *C07H 7/033* (2013.01); *B01J 21/04* (2013.01); *B01J 21/063* (2013.01)

(58) Field of Classification Search
None
See application file for complete search history.

(56) References Cited

U.S. PATENT DOCUMENTS 7,982,031 B2   7/2011   Kowalczyk et al.
2008/0187984 A1   8/2008   Schroeder et al.

OTHER PUBLICATIONS

International Search Report from corresponding PCT application No. PCT/NL2013/050234 dated Jun. 18, 2013.

*Primary Examiner* — Yevegeny Valenrod
(74) *Attorney, Agent, or Firm* — McDermott Will & Emery LLP

(57) ABSTRACT

Disclosed is the oxidation of uronic acids, such as galacturonic acid, to the corresponding aldaric acids (characterized by the formula HOOC—(CHOH)n-COOH, with n being an integer of from 1 to 5) such as galactaric acids. The starting material comprising the uronic acid is subjected to oxygen under the influence of a supported gold catalyst and in the presence of a base. The oxidation occurs in good selectivity and yield, under unexpectedly mild conditions. A source of galacturonic acids is pectin, such as that derived from sugar beet pulp.

10 Claims, No Drawings

CATALYTIC OXIDATION OF URONIC ACIDS TO ALDARIC ACIDS

RELATED APPLICATIONS

This application is the U.S. National Stage of International Application No. PCT/NL2013/050234, filed Mar. 28, 2013, published in English, and claims the benefit of European Application Number 12163081.8, filed on Apr. 4, 2012, the entire teachings of the above applications are incorporated herein by reference.

FIELD OF THE INVENTION

The invention pertains to the synthesis of aldaric acids and derivatives thereof, from uronic acids. Also, the invention pertains to a method of producing galactaric acid from sugar beet pulp.

BACKGROUND OF THE INVENTION

Aldaric acids are a group of sugar acids, where the terminal hydroxyl or aldehyde groups of the sugars have been replaced by terminal carboxylic acids. These acids are characterized by the formula HOOC—$(CHOH)_n$—COOH, with n being an integer of from 1 to 5. These dicarboxylic acids, on account of their combined functionalities, are interesting chemicals. E.g., as sequestering agents, corrosion inhibitors or monomers for making polymers made on the basis of dicarboxylic acids, such as polyesters or polyamides. Preferred aldaric acids are those wherein n is an integer of from 3 to 5. Aldaric acids of particular interest are those derived from C5 and C6 sugars, like xylaric acid, glucaric acid, mannaric acid, gularic acid and iduronic acid. An aldaric acid of particular interest is galactaric acid, the aldaric acid corresponding to the sugar galactose. Applications for galactaric acid range from sequestering agents (Kohn et al. Collect. Czech. Chem. Commun. 1986, 1150) to building blocks for polymers (e.g. Moore & Bunting Polym. Sci. Technol., Adv. Polym. Synth., 51). Other aldaric acids of particular interest are glucaric acid, mannaric acid and gularic acid, aldaric acids that can be obtained from the carbohydrate fraction of biomass sources including pectins and a variety of different seaweeds.

Aldaric acids can be prepared by the oxidation of the corresponding aldoses into the aldaric acids. To this end in literature the nitric acid oxidation of aldoses into aldaric acid is well known, as well as the TEMPO mediated oxidation of aldoses into aldaric acids. However, for these procedures a double oxidation of both the aldehyde group as well as the terminal hydroxyl group is required resulting in relatively low yields, and numerous side-products.

The background art includes some examples on the oxidation of galacturonic acid to galactaric acid. According to FR 2699937 galacturonic acid can be oxidized to galactaric acid using an electrochemical cell giving galactaric acid in 80% yield (90% conversion, 90% selective) after 7 h at 55-58° C., in 1M concentration. Rangappa et al. (J. Carbohydr. Chem. 1997, 359) reported the oxidation of galacturonic acid by using excess sodium N-chlorobenzenesulfonamide in alkaline medium, while Shashikala and Rangappa (J. Carbohydr. Chem. 2002, 491) reported the oxidation of galacturonic acid by using excess sodium N-bromoarylsulfonamides in alkaline medium. According to WO 2010/072902 via a microbial host strain expressing uronate dehydrogenase enzyme (EC 1.1.1.203), galacturonic acid is converted into galactaric acid. Here a typical incubation time is 3 to 5 days to convert 1-2 wt % of galacturonic acid into galactaric acid (mucic acid) without mentioning selectivity or isolated yield.

The oxidation of glucuronic acid is described in U.S. Pat. No. 6,518,419 by using peracids as an oxidant. Alternatively hydrogen peroxide can be used to form the peracid in situ. In this procedure TEMPO in combination with a halide, preferably a bromide, act as the catalyst. D-glucaric acid was isolated as the K-salt in 62% yield.

In US 20080187984 the oxidation of glucuronic acid to glucaric acid is performed via enzymatic procedures. Three different polypeptides are suggested: peptides with non-specific hexose oxidase activity (EC 1.1.3.5), peptides with aldehyde dehydrogenase [NAD(P)] activity (EC 1.2.1.5, EC 1.2.1.3 (NAD), EC 1.2.1.4 (NADP) or by a polypeptide having aldehyde oxidase activity (EC 1.2.3.1). No isolated yields are reported.

In the same patent US 20080187984 it is suggested that the oxidation can be performed via a chemical step by using molecular oxygen and a catalyst. The patent includes an example where glucuronic acid is oxidized with molecular oxygen and a 5% palladium on carbon catalyst. This procedure requires high catalyst loadings (10 g Pd/C for the conversion of 5 g glucuronic acid) in order to obtain reasonable selectivity's. A product yield of 90% was reported based on HPLC analysis. This work was based upon the work described in U.S. Pat. No. 5,817,870, were it was shown that high metal loadings (>10 percent by weight) improve the selectivity for oxidation reactions.

None of these methods is attractive for commercial production. The background also includes examples of the oxidation of aldoses to the corresponding aldonic acids over Au based catalysts. U.S. Pat. No. 7,892,031 describes the oxidation of aldoses like glucose and lactose over Au/TiO2 catalysts at 40 C and pH 9 in high selectivity. The oxidation of alduronic acids into aldaric acids is not described.

Biorefineries serve to conduct the sustainable processing of biomass into a spectrum of marketable biobased products and bioenergy. A biorefinery is an installation that can process biomass into multiple products using an array of processing technologies. In general, biomass coming from plants, will result in streams based on lignin, cellulose, and hemicellulose, respectively. Hemicelluloses can be removed from biomass, e.g. by treatment with hot pressurized water. This results in formation of water soluble oligomeric and monomeric sugars and their dehydration products such as furfural and hydroxymethyl furfural. Another source of hemicelluloses is in the agro-food industry. Whilst hemicelluloses, in theory, are a source of a wide variety of useful chemicals, it is desired to find methods to make better use of this potential, by providing economically attractive processes to harvest such chemicals therefrom. A particular interesting hemicellulosic feedstock from the agro-food industry comprises sugar beet pulp, a byproduct of the sugar beet industry. Sugar beet pulp contains a high content of pectic substances, being composed of arabinose and galacturonic acid as the main monomers. Other sources of pectins are alls kind of different fruits, including e.g. apples, carrots, cherries and citrus fruits, especially citrus peels. Another potential source of uronic acids is being formed by alginates. A large variety of seaweeds including red and brown seaweeds like *Laminaria digitata, Saccharina latissima* and *Ulva lactuca* contain huge amounts of alginates being composed of mannuronic acid and guluronic acid as the composing monomers; after hydrolysis of the alginates such monomers can be used as feedstock for the production of aldaric acids.

It would be desired to provide a process enabling the unlocking of the chemical potential present in the form of uronic acids in hemicellulosic streams.

SUMMARY OF THE INVENTION

In order to address one or more of the foregoing desires, the invention, in one aspect, provides a process for the preparation of an aldaric acid by the oxidation of the corresponding uronic acid, wherein a starting material comprising the uronic acid is subjected to oxygen under the influence of a supported gold catalyst and in the presence of a base. In another aspect, the invention presents the use of an uronic acid as a starting material for the production of the corresponding aldaric acid, wherein the uronic acid is subjected to oxygen under the influence of a supported gold catalyst, and in the presence of a base.

In a further aspect, the invention provides the use of sugar beet pulp or citrus fruits as a starting material for the oxidation of galacturonic acid into galactaric acid.

In a still further aspect the invention provides the use of pectin rich sources like orange peels, for the oxidation of glucuronic acid into glucaric acid, In a further aspect the invention provides the use of glucuronic acid rich sources such as hyaluronic acids or glycosaminoglycans, for the oxidation of glucuronic acid into glucaric acid.

In yet another aspect, the invention provides the use of alginate containing seaweeds for the oxidation of mannuronic acid and guluronic acid into mannaric acid and gularic acid, respectively.

DETAILED DESCRIPTION OF THE INVENTION

In a broad sense, the invention is based on the insight that the versatile chemical potential available as uronic acids in, e.g., hemicellulosic and pectin rich waste streams or seaweeds, can be put to use by catalytic oxidation. To this end, the inventors have judiciously identified supported gold catalysts to catalyze the oxidation.

The starting material for the catalytic oxidation of the invention can be the uronic acid itself. Preferred uronic acids include: galacturonic acid, glucuronic acid, mannuronic acid, iduronic acid, gularic acid and most preferably galacturonic acid. The invention provides an efficient, and highly selective catalytic oxidation of the uronic acid to the corresponding aldaric acid, e.g. from galacturonic acid to galactaric acid. To this end, supported gold catalysts are used. Such catalyst comprise support of a metal oxide, e.g. $TiO_2$ or $Al_2O_3$, or other materials customary in the art of providing supported catalysts for heterogeneous catalysis.

The metal oxide support generally is a catalyst support made of at least one oxide of a main group or transition metal or metalloid, including compounds which comprise more than one metal and/or metalloid. Preference is given in this connection to oxides of metals or metalloids of main group 2 of the Periodic Table, such as MgO, CaO or BaO, oxides of metals or metalloids of main group 3 of the Periodic Table, such as $Al_2O_3$ or lanthanoid oxides or oxides of metals or metalloids of main group 4 (IVA or IVB) of the Periodic Table, such as $TiO_2$, $ZrO_2$, $SnO_2$, or $SiO_2$. Also $Fe_2O_3$ can be employed. The compounds having more than one metal and/or metalloid are preferably silicates, especially aluminosilicates. The gold comprises metallic gold, dispersed onto the support, preferably as nanoparticles.

As an alternative for the metal oxide supports, the gold can be supported on carbon supports, e.g. activated carbons, carbon blacks, graphites, carbon nanotubes, carbon nanofibers, etc.

The support will generally comprise, in weight percentages relative to the support, of from 0.1% to 5% gold. Preferred percentages are 0.1% to 0.5%. The metal oxide-supported gold catalyst is preferably employed in the form of a powder or granules.

The gold nanoparticles generally have a diameter of below 10 nm, preferably of below 6 nm and most preferably of from 1 to 2 nm. The metal oxide-supported gold catalysts used according to the invention can be prepared, i.e. gold can be deposited in the form of nanoparticles on the metal oxide support materials, for example by employing precipitation methods where the gold is deposited in the form of oxidic/hydroxic gold precursors by precipitation on the metal oxide support, or is precipitated together with a precursor of the metal oxide support. Au can also be introduced in the sol-gel synthesis of the support, for example of an earth metal oxide or a transition metal oxide. Also known are impregnation with gold solutions and the application of Au colloids to supports using various polymers as colloid stabilizers. Suitable methods for preparing metal oxide-supported gold catalysts include for example precipitation methods, deposition-precipitation methods and methods for chemical deposition from the gas phase (CVD methods) and are described inter alia in Prati and Martra, Gold Bulletin, 32(3) (1999), 96-101; Wolf and Schuth, Applied Catalysis A: General., 226 (2002), 1-13, and Berndt et al., Applied Catalysis A: General, 6442 (2003), 1-11.

The uronic acid is subjected to oxygen in order to affect the oxidation. Whilst the oxygen can be in the form of air, it is preferred that the catalytic oxidation is conducted under the influence of an oxygen-containing gas-stream comprising at least 40% oxygen, preferably at least 60% oxygen. More preferably, the oxygen-containing gas-stream is oxygen having a purity of from 90%-100%. An advantage of the invention, is that it also works well with relatively cheap compressed air.

The oxidation can be conducted under relatively mild conditions. Preferred temperatures range from 0° C. to 50° C., preferably from 15° C. to 35° C., and most preferably at room temperature. The low temperature is an unexpected advantage as compared to other oxidations using supported gold catalysts.

The oxidation is conducted for a suitable period of time, generally more than 0.5 hours and less than 24 hours, preferably 1-5 hours, more preferably 2-3 hours.

The pH during the oxidation is generally 7-11, preferably 9-12. A base is present in generally 0.5 to 5 eq., preferably 1 eq. to 1.5 eq. The method of the invention is generally conducted at atmospheric pressure, although other pressures (range 1-10 bar) can also be employed.

The invention preferably pertains to a process for the preparation of galactaric acid by the oxidation of galacturonic acid using the above-described method using a supported gold catalyst. By further preference the galacturonic acid is isolated from a biowaste material comprising pectin hydrolyzates.

In this respect, the invention also pertains to the catalytic oxidation of pectin-constituents (galacturonic acid and arabinose) to aldaric acids (galactaric acid) and aldonic acids (arabinonic acid) with molecular oxygen or air, using supported gold catalysts, under mild conditions as mentioned above.

The process of the invention can be conducted in a manner generally known to the skilled person, in such reactors as can normally be used for other catalytic oxidation processes.

The aldaric acids produced can be further worked up (separated, purified) using techniques generally known in the art. This includes, e.g., precipitation of the acid (e.g. mucic acid), or the use of ion exchange columns.

In summary, the invention provides the oxidation of uronic acids, such as galacturonic acid, to the corresponding aldaric acids, such as galactaric acids. Use is made of a supported gold catalyst. The oxidation occurs in good selectivity and yield, under unexpectedly mild conditions. A source of galacturonic acids is pectins, such as from sugar beet pulp.

By virtue of the process of the invention, the invention opens up the use, and particularly in a more economical or beneficial manner, of various biobased starting materials for the production of various desired chemicals.

Thus, in one aspect, the invention includes the use of uronic acids as a starting material for the production of an aldaric acid, wherein the uronic acid is subjected to oxygen under the influence of a supported gold catalyst, and in the presence of a base. In another aspect, the invention includes the use of sugar beet pulp or citrus fruits as a starting material for the oxidation of galacturonic acid into galactaric acid, or glucuronic acid into glucaric acid, by subjecting said starting materials to oxygen under the influence of a supported gold catalyst, and in the presence of a base. In yet another aspect, the invention provides the use of seaweeds as a starting material for the oxidation of mannuronic acid and guluronic acid into mannaric acid and gularic acid, by subjecting said starting material to oxygen under the influence of a supported gold catalyst, and in the presence of a base.

The invention also presents a novel use for supported gold catalysts. Accordingly, in this aspect of the invention, the use is presented of a supported gold catalyst for the oxidation of a starting material selected from the group consisting of uronic acid, pectin hydrolyzates, sugar beet pulp, citrus fruits, and seaweeds. In this use, the starting material is subjected to oxygen under the influence of said supported gold catalyst and in the presence of a base.

Preferably, the aforementioned uses of various starting materials, and the novel use of supported gold catalysts, are realized by carrying out the oxidation by a process according to any of the embodiments described hereinbefore.

The invention will be illustrated hereinafter with reference to the following non-limiting examples. Percentages are indicated by weight.

General Procedure

Reactions were performed in a Parr MRS5000 parallel reactor system (6*75 mL, Hastelloy C-276) equipped with glass liner and magnetic stirrer. The reagents were dissolved in $NaOD/D_2O$ or $NaOH/H_2O$ and the resulting clear solutions were transferred to the glassliners. Catalyst was added (the catalyst extrudates were pulverized in a mortar to give a fine powder) and the reactors were closed. Reactors were flushed 3 times with $O_2$ or synthetic air at 3 bar. Next the reactors were pressurized to the desired $O_2$ or synthetic air pressure. Subsequently, magnetic stirring (500 rpm) was started. After the desired reaction time, samples of the reaction mixture were taken to determine the conversion. Samples were filtered over a 0.45 μm Minisart NML syringe filter to remove the catalyst and $^1$H-NMR was measured without any further work-up.

Example 1

Oxidation of D-Galacturonic Acid Sodium Salt with 1 eq. Base and 1.2 wt % $Au/TiO_2$ (0.2 mol % Au) Under 1 Bar $O_2$ Pressure The reaction was performed as described in the general procedure, using a 75 mL Hastelloy C-276 reactor in a Parr MRS5000 parallel reactor system. In a glass liner equipped with a stirring bar, D-galacturonic acid sodium salt (215 mg, 1 mmol) was dissolved in 10 mL $NaOD/D_2O$ (0.1 M) to give a clear colorless solution. 36 mg 1.2 wt % $Au/TiO_2$ (2.18 μmol Au) was added and the reactor was closed. After flushing the reactor 3× with 3 bar oxygen, the reactor was placed under 1 bar oxygen and stirring was started at 500 rpm. The reaction was performed at room temperature and was monitored after 1, 3 and 5 h by taking 1 mL samples. Samples were filtered over a 0.45 μm Minisart NML syringe filter to remove the catalyst and $^1$H-NMR was measured without any further work-up to determine the conversions. The reaction was completed for ~95% after 1 h, >99% conversion of the starting material was achieved after 3 h. After 5 h reaction time, D-galactaric acid disodium salt was still the main product (>97%) along with trace amounts (<3%) side products.

Example 2

Oxidation of D-Galacturonic Acid Sodium Salt with 1 eq. Base and 1.2 wt % $Au/TiO_2$ (0.2 mol % Au) Under 5 Bar Sythetic Air Pressure The reaction was performed as described in the general procedure, using a 75 mL Hastelloy C-276 reactor in a Parr MRS5000 parallel reactor system. In a glass liner equipped with a stirring bar, D-galacturonic acid sodium salt (216 mg, 1 mmol) was dissolved in 10 mL $NaOD/D_2O$ (0.1 M) to give a clear colorless solution. 36 mg 1.2 wt % $Au/TiO_2$ (2.18 μmol Au) was added and the reactor was closed. After flushing the reactor 3× with 5 bar synthetic air, the reactor was placed under 5 bar synthetic air and stirring was started at 500 rpm. The reaction was performed at room temperature and was monitored after 1, 3 and 5 h by taking 1 mL samples. Samples were filtered over a 0.45 μm Minisart NML syringe filter to remove the catalyst and $^1$H-NMR was measured without any further work-up to determine the conversions. The reaction was completed for >80% after 1 h, >99% conversion of the starting material was achieved after 3 h. After 5 h reaction time, D-galactaric acid disodium salt was still the main product (>97%) along with trace amounts (<3%) side products.

Example 3

Oxidation of D-Galacturonic Acid Sodium Salt with 1 eq. Base and 1.2 wt % $Au/TiO_2$ (0.2 Mol % Au) Under Atmospheric $O_2$ Pressure A 100 mL 3-necked round bottom flask equipped with gas inlet, magnetic stirring bar and gas outlet was placed on an magnetic stirrer. D-galacturonic acid sodium salt (436 mg, 2 mmol) was dissolved in 20 mL $NaOD/D_2O$ (0.1 M) to give a clear colorless solution. 72 mg 1.2 wt % $Au/TiO_2$ (4.36 μmol Au) was added and stirring was started at 800 rpm. At room temperature, $O_2$ (ca 100 mL/min) was bubbled through the reaction mixture via the gas inlet. The reaction was monitored after 3 and 19 h by taking 1 mL samples. Samples were filtered over a 0.45 μm Minisart NML syringe filter to remove the catalyst and $^1$H-NMR was measured without any further work-up to determine the conversions. The reaction was completed after 3 h, D-galactaric acid disodium salt was the main product (>97%) along with trace amounts (<3%) side products. After 19 h the product composition was not changed, showing that the product was stable under the applied conditions.

Example 4

Oxidation of D-Galacturonic Acid Sodium Salt with 1 eq. Base and 1.2 wt % Au/TiO$_2$(0.2 Mol % Au) Using Synthetic Air Under Atmospheric Pressure A 100 mL 3-necked round bottom flask equipped with gas inlet, magnetic stirring bar and gas outlet was placed on an magnetic stirrer. D-galacturonic acid sodium salt (432 mg, 2 mmol) was dissolved in 20 mL NaOD/D$_2$O (0.1 M) to give a clear colorless solution. 72 mg 1.2 wt % Au/TiO$_2$ (4.36 μmol Au) was added and stirring was started at 800 rpm. At room temperature, synthetic air (ca 100 mL/min) was bubbled through the reaction mixture via the gas inlet. The reaction was monitored after 1, 3 and 5 h by taking 1 mL samples. Samples were filtered over a 0.45 μm Minisart NML syringe filter to remove the catalyst and $^1$H-NMR was measured without any further work-up to determine the conversions. The reaction was completed after 3 h, D-galactaric acid disodium salt was the main product (>97%) along with trace amounts (<3%) side products. After 5 h the product composition was not changed, showing that the product was stable under the applied conditions.

Example 5

Oxidation of D-Galacturonic Acid Sodium Salt Under pH-Stat Conditions and 1.2 wt % Au/TiO$_2$ (0.2 Mol % Au) Using Synthetic Air Under Atmospheric Pressure A 50 mL 3-necked round bottom flask equipped with gas inlet and magnetic stirring bar was placed on an magnetic stirrer. A pH-STAT equipped with a titration solution of 4 M NaOH in water was used to keep pH constant at pH 10 during the reaction. D-galacturonic acid sodium salt (4.32 g, 20 mmol) was dissolved in 15 mL demineralized water to give a clear colorless solution. 864 mg 1.2 wt % Au/TiO$_2$ (0.04 mmol Au) was added and stirring was started at 800 rpm. At room temperature, synthetic air (ca 100 mL/min) was bubbled through the reaction mixture via the gas inlet. The pH of the reaction was set to a constant value of pH 10 and the titration was started. During the reaction, base was added slowly, indicating the formation of the desired mucic acid. After 48 h the consumption of base stopped. The total volume of added 4 M NaOH was 3.78 mL (76% of theoretical amount of base needed for the production of 20 mmol mucic acid disodium salt). A 0.1 mL sample was filtered over a 0.45 μm Minisart NML syringe filter to remove the catalyst and after addition of 0.9 mL D$_2$O $^1$H-NMR was measured without any further work-up to determine the conversion. According to $^1$H-NMR the conversion of the starting material was complete. Mucic acid disodium salt was the main product, with some unknown side products.

Example 6

Oxidation of D-Galacturonic Acid Sodium Salt with 1 eq. Base and 1.2 wt % Au/TiO$_2$ (0.2 Mol % Au) Under 1 Bar O$_2$ Pressure. Isolation of Galactaric Acid Via Precipitation The reaction was performed as described in the general procedure, using 6×75 mL Hastelloy C-276 reactors in a Parr MRS5000 parallel reactor system. D-galacturonic acid sodium salt (5.184 g, 24 mmol) was dissolved in 240 mL NaOH/H$_2$O (0.1 M) to give a clear colorless solution. The solution was transferred to the 6 reactors (6×40 mL), equipped with stirring bars. To each reactor was added 144 mg 1.2 wt % Au/TiO$_2$ (6×8.77 μmol Au) and the reactors were closed. After flushing the reactors 3× with 3 bar oxygen, the reactors were placed under 1 bar oxygen and stirring was started at 500 rpm. Reactions were performed at room temperature for 4 h. After opening of the reactors, the reaction mixtures were pooled together and the catalyst was filtered off under vacuum over celite on a type 3 glass filter, to give a clear slightly yellow filtrate. The filtrate was acidified to pH 3 using 48 mL HCl (1 M). After the first few drops of HCl (1 M) the yellow color disappeared, the filtrate started to become turbid and the pH dropped from pH=11-12 to pH=4-5. After complete addition, the pH dropped to pH 2.4. After 1 night in the refrigerator the pH was ~3. The white precipitate was filtered off under vacuum on a type 4 glass filter, washed with water (2×20 mL) and dried overnight in a vacuum oven at 40° C. Yield: 4.010 g (79.6 mol %) white solid.

$^1$H/$^{13}$C-NMR (in DMSO-D$_6$) and FT-IR showed galactaric acid as the only product in high purity (>99%).

Example 7

Control Experiment, Oxidation of D-Galacturonic Acid Sodium Salt in the Absence of Base, Using 1.2 wt % Au/TiO$_2$ (0.2 Mol % Au) Under 1 Bar O$_2$ Pressure The reaction was performed as described in the general procedure, using a 75 mL Hastelloy C-276 reactor in a Parr MRS5000 parallel reactor system. In a glass liner equipped with a stirring bar, D-galacturonic acid sodium salt (216 mg, 1 mmol) was dissolved in 10 mL D$_2$O to give a clear colorless solution. 36 mg 1.2 wt % Au/TiO$_2$ (2.18 μmol Au) was added and the reactor was closed. After flushing the reactor 3× with 3 bar oxygen, the reactor was placed under 1 bar oxygen and stirring was started at 500 rpm. The reaction was performed at room temperature and was monitored after 1, 3 and 5 h by taking 1 mL samples. Samples were filtered over a 0.45 μm Minisart NML syringe filter to remove the catalyst and $^1$H-NMR was measured without any further work-up to determine the conversions. No reaction was observed, and no side products were formed.

Example 8

Control Experiment, Oxidation of D-Galacturonic Acid Sodium Salt with 10 eq. Base in the Absence of Catalyst Under 1 Bar O$_2$ Pressure The reaction was performed as described in the general procedure, using a 75 mL Hastelloy C-276 reactor in a Parr MRS5000 parallel reactor system. In a glass liner equipped with a stirring bar, D-galacturonic acid sodium salt (215 mg, 1 mmol) was dissolved in 10 mL NaOD/D$_2$O (1.0 M) to give a clear colorless solution. The reactor was closed and flushed 3× with 3 bar oxygen, the reactor was placed under 1 bar oxygen and stirring was started at 500 rpm. The reaction was performed at room temperature and was stopped after 5 h. A 1 mL sample was taken and $^1$H-NMR was measured without any further work-up to determine the conversion. No reaction was observed, and no side products were formed.

Example 9

Control Experiment, Oxidation of D-Galacturonic Acid Sodium Salt with 2 eq. Base in the Presence of TiO$_2$ Support, Under 3 Bar O$_2$ Pressure The reaction was performed as described in the general procedure, using a 75 mL Hastelloy C-276 reactor in a Parr MRS5000 parallel reactor system. In a glass liner equipped with a stirring bar, D-galacturonic acid sodium salt (216 mg, 1 mmol) was dissolved in 10 mL NaOD/D$_2$O (0.2 M) to give a clear colorless solution. 36 mg TiO$_2$ was added and the reactor was closed. The reactor was flushed 3× with 3 bar oxygen, the reactor was placed under 3 bar oxygen and stirring was started at 500 rpm. The reaction was performed at room temperature and was stopped after 5 h. A 1 mL sample was filtered over a 0.45 µm Minisart NML syringe filter to remove the TiO$_2$ support and $^1$H-NMR was measured without any further work-up to determine the conversion. No formation of galactaric acid was observed, and only a small amount (~7%) of side products were formed.

Example 10

Oxidation of D-Galacturonic Acid Sodium Salt with 1 eq. Base Under 1 Bar O$_2$ Pressure. Use of Gold on Various Supports (ZnO, Al$_2$O$_3$) and Other Metals (Pd, Pt and Ru) on Al$_2$O$_3$ The reaction was performed as described in the general procedure, using 75 mL Hastelloy C-276 reactors in a Parr MRS5000 parallel reactor system. In a glass liner equipped with a stirring bar, D-galacturonic acid sodium salt (216 mg, 1 mmol) was dissolved in 10 mL NaOD/D$_2$O (0.1 M) to give a clear colorless solution. Catalysts were added (all using the same mol % metal loading as in example 1 above) and the reactors were closed. After flushing the reactors 3× with 3 bar oxygen, the reactors were placed under 1 bar oxygen and stirring was started at 500 rpm. The reactions were performed at room temperature and were monitored after 3 h by taking 1 mL samples. Samples were filtered over a 0.45 µm Minisart NML syringe filter to remove the catalyst and $^1$H-NMR was measured without any further work-up to determine the conversions.

All Au catalysts were active and gave >95% conversion with >96% selectivity. Under these mild conditions, the other Al$_2$O$_3$ supported metals (Pd, Pt and Ru) gave no conversion of the starting material.

The results are depicted in Table 1 below.

TABLE 1

| Catalyst type | Amount of catalyst (mg) | Catalyst loading (mol % metal) | Result (conversion (%) and selectivity (%)) |
|---|---|---|---|
| Au/ZnO | 48 | 0.22 | >95% conv.; >96% select. |
| Au/Al$_2$O$_3$ | 43 | 0.22 | >99% conv.; >96% select. |
| Pd/Al$_2$O$_3$ | 4.7 | 0.22 | 0% conv. |
| Pt/Al$_2$O$_3$ | 8.6 | 0.22 | 0% conv. |
| Ru/Al$_2$O$_3$ | 4.5 | 0.22 | 0% conv. |

Example 11

Oxidation of a Mixture of D-Galacturonic Acid Sodium Salt and L-Arabinose with 1 eq. Base and 1.2 wt % Au/TiO$_2$ (0.2 Mol % Au) Under 1 Bar O2 Pressure The reaction was performed as described in the general procedure, using a 75 mL Hastelloy C-276 reactor in a Parr MRS5000 parallel reactor system. In a glass liner equipped with a stirring bar, a mixture of D-galacturonic acid sodium salt (110 mg, 0.5 mmol) and L-arabinose (75 mg, 0.5 mmol) was dissolved in 10 mL NaOD/D$_2$O (0.1 M) to give a clear colorless solution. 38 mg 1.2 wt % Au/TiO$_2$ (2.32 µmol Au) was added and the reactor was closed. After flushing the reactor 3× with 3 bar oxygen, the reactor was placed under 1 bar oxygen and stirring was started at 500 rpm. The reaction was performed at room temperature and was monitored after 5 h by taking a 1 mL sample. The sample was filtered over a 0.45 µm Minisart NML syringe filter to remove the catalyst and $^1$H-NMR was measured without any further work-up to determine the conversion. The reaction was completed for >85% after 5 h. L-arabinonic acid sodium salt and D-galactaric acid disodium salt were the main products.

Example 12

Oxidation of D-Glucuronic Acid Sodium Salt Monohydrate with 1 eq. Base and 1.2 wt % Au/TiO$_2$ (0.2 Mol % Au) Under 1 Bar O$_2$ Pressure The reaction was performed as described in the general procedure, using a 75 mL Hastelloy C-276 reactor in a Parr MRS5000 parallel reactor system. In a glass liner equipped with a stirring bar, D-glucuronic acid sodium salt monohydrate (235 mg, 1 mmol) was dissolved in 10 mL NaOD/D$_2$O (0.1 M) to give a clear colorless solution. 36 mg 1.2 wt % Au/TiO$_2$ (2.18 µmol Au) was added and the reactor was closed. After flushing the reactor 3× with 3 bar oxygen, the reactor was placed under 1 bar oxygen and stirring was started at 500 rpm. The reaction was performed at room temperature and was monitored after 5 h by taking a 1 mL sample. The sample was filtered over a 0.45 µm Minisart NML syringe filter to remove the catalyst and $^1$H-NMR was measured without any further work-up to determine the conversion. The reaction was completed for ~85% after 5 h, D-glucaric acid &sodium salt was the main product (>98%) along with trace amounts (<2%) side products.

The examples are summarized in Table 2.

TABLE 2

| Example | Substrate | Catalyst (0.2 mol %) | Base (eq.) | Pressure (bar) | Time (h) | Conv/Select |
|---|---|---|---|---|---|---|
| 1 | 1 mmol GA | Au/TiO2 | 1 (NaOD) | 1 (O2) | 1, 3, 5 | >99, 97 (3 h) |
| 2 | 1 mmol GA | Au/TiO2 | 1 (NaOD) | 5 (AIR) | 1, 3, 5 | >99, 97 (3 h) |
| 3 | 2 mmol GA | Au/TiO2 | 1 (NaOD) | Atm. (O2) | 3, 19 | >99, 97 (3 h) |
| 4 | 2 mmol GA | Au/TiO2 | 1 (NaOD) | Atm. (Air) | 1, 3, 5 | >99, 98 (3 h) |
| 5 | 20 mmol GA | Au/TiO2 | STAT | Atm. (Air) | 48 | >99, unknown |

TABLE 2-continued

| Example | Substrate | Catalyst (0.2 mol %) | Base (eq.) | Pressure (bar) | Time (h) | Conv/Select |
|---|---|---|---|---|---|---|
| 6 | 24 mmol GA | Au/TiO2 | 1 (NaOH) | 1 (O2) | 4 | 80% isolated yield |
| 7 | 1 mmol GA | Au/TiO2 | 0 (D2O) | 3 (O2) | 1, 3, 5 | No conversion (5 h) |
| 8 | 1 mmol GA | — | 10 (NaOD) | 3 (O2) | 5 | No conversion (5 h) |
| 9 | 1 mmol GA | TiO2 | 2 (NaOD) | 3 (O2) | 5 | No conversion, small amount side products (5 h) |
| 10 | 1 mmol GA | Au/ZnO | 1 (NaOD) | 1 (O2) | 3 | >95, 96 (3 h) |
|  | 1 mmol GA | Au/Al2O3 | 1 (NaOD) | 1 (O2) | 3 | >99, 96 (3 h) |
|  | 1 mmol GA | Pd/Al2O3 | 1 (NaOD) | 1 (O2) | 3 | 0 (3 h) |
|  | 1 mmol GA | Pt/Al2O3 | 1 (NaOD) | 1 (O2) | 3 | 0 (3 h) |
|  | 1 mmol GA | Ru/Al2O3 | 1 (NaOD) | 1 (O2) | 3 | 0 (3 h) |
| 11 | GA + L-Ar (2 x 0.5 mmol) | Au/TiO2 | 1 (NaOD) | 1 (O2) | 5 | ~85%, selective |
| 12 | 1 mmol GlucA | Au/TiO2 | 1 (NaOD) | 1 (O2) | 3, 5 | ~85%, 97 (5 h) Reaction incomplete |

The invention claimed is:

1. A process for the preparation of an aldaric acid by the oxidation of the corresponding uronic acid, wherein a starting material comprising the uronic acid is subjected to oxygen under the influence of a supported gold catalyst and in the presence of a base.

2. A process according to claim 1, wherein the oxygen is in the form of air.

3. A process according to claim 1, wherein the oxygen is in the form of an oxygen-containing gas-stream comprising at least 40% oxygen, preferably at least 60% oxygen.

4. A process according to claim 3, wherein the oxygen-containing gas stream is oxygen-enriched air.

5. A process according to claim 1, wherein the uronic acid is selected from the group consisting of galacturonic acid, glucuronic acid, mannuronic acid, guluronic acid, and mixtures thereof.

6. A process according to claim 1, wherein the starting material further comprises at least one aldose.

7. A process according to claim 5, wherein the starting material comprises a pectin hydrolyzate, preferably sourced from sugar beet pulp.

8. A process according to claim 1, wherein the oxidation is carried out at a temperature in the range of from 0° C. to 50° C., preferably from 15° C. to 35° C.

9. A process according to claim 1, followed by the purification of the aldaric acid.

10. A process according to claim 1, wherein the aldaric acid is selected from the group consisting of galactaric acid, xylaric acid, glucaric acid, mannaric acid, gularic acid and iduronic acid.

* * * * *